(12) United States Patent
Chen

(10) Patent No.: US 6,200,475 B1
(45) Date of Patent: Mar. 13, 2001

(54) METHOD OF CONVERTING ORGANIC WASTE BY THERMOPHILIC FERMENTATION

(76) Inventor: Shen-Yuan Chen, 19506 Pilario St., Rowland Height, CA (US) 91748

( * ) Notice: Subject to any disclaimer, the term of this patent is extended or adjusted under 35 U.S.C. 154(b) by 0 days.

(21) Appl. No.: 09/399,391

(22) Filed: Sep. 20, 1999

(51) Int. Cl.$^7$ .................................. C02F 3/10; B09B 3/00
(52) U.S. Cl. ..................... 210/613; 210/615; 210/616; 210/620; 210/629; 435/176; 435/177; 435/180; 435/262.5; 71/9; 71/14; 71/21; 71/23
(58) Field of Search ..................... 210/612, 613, 210/620, 629, 615, 616, 617; 435/262, 262.5, 176, 177, 180, 268; 71/9, 18, 21, 14, 23

(56) References Cited

U.S. PATENT DOCUMENTS

| | | | |
|---|---|---|---|
| 3,285,732 | * 11/1966 | Schulze . | |
| 3,462,275 | 8/1969 | Bellamy et al. | ............................ 99/9 |
| 3,838,198 | 9/1974 | Bellamy et al. | ........................ 426/53 |
| 3,864,247 | 2/1975 | Fuchs | ..................................... 210/12 |
| 3,963,470 | * 6/1976 | Haug . | |
| 4,132,638 | 1/1979 | Carlsson | ................................... 210/7 |
| 4,284,508 | * 8/1981 | Jewell . | |
| 4,292,328 | 9/1981 | Choulthard et al. | ...................... 426/2 |
| 4,302,546 | * 11/1981 | Schlichting, Jr. . | |
| 4,321,141 | * 3/1982 | Messing . | |
| 4,342,836 | * 8/1982 | Harvey . | |
| 4,414,335 | * 11/1983 | Kipp, Jr. . | |
| 4,551,250 | * 11/1985 | Morper et al. . | |
| 5,100,553 | * 3/1992 | Nomura et al. . | |
| 5,169,782 | * 12/1992 | Murphy et al. . | |
| 5,180,495 | 1/1993 | Thller et al. | .......................... 210/630 |
| 5,185,255 | 2/1993 | Endo et al. | ........................... 435/174 |
| 5,240,611 | 8/1993 | Burton | ................................. 210/603 |
| 5,248,602 | * 9/1993 | Schmid et al. . | |
| 5,525,228 | * 6/1996 | Dague et al. . | |
| 5,534,042 | * 7/1996 | Tsuchida . | |
| 5,595,893 | 1/1997 | Pometto, III et al. | ............... 435/136 |
| 5,702,499 | 12/1997 | Timmernga | ................................ 71/9 |
| 5,728,577 | 3/1998 | Kuriyama | ............................ 435/299 |
| 5,733,454 | * 3/1998 | Cummings . | |
| 5,810,903 | 9/1998 | Branconnier et al. | ..................... 71/9 |
| 5,863,789 | 1/1999 | Komatsu et al. | .................... 435/262 |
| 5,958,756 | * 9/1999 | Reynell . | |

* cited by examiner

Primary Examiner—David A. Simmons
Assistant Examiner—Fred Prince
(74) Attorney, Agent, or Firm—Raymond Y. Chan; David and Raymond Patent Group

(57) ABSTRACT

A method of converting organic waste to a useful end product by aerobic thermophilic fermentation process within a short period of time, includes the steps of mixing the organic waste that naturally contains microorganisms with the porous material as a fermentation medium in a mixing digester to form a waste mixture, providing an external heat source to transfer heat into the waste mixture of the organic waste and the porous material, maintaining the waste mixture at a thermophilic temperature to create microbial symbiosis and mutualism reaction to proliferate and grow beneficial thermophilic microorganisms between the porous material and microorganisms that naturally present in the organic waste and allowing whereby the microbial reaction to accelerate the organic waste fermentation and decomposition speed and decompose the organic waste into the usefil end product within a short period of time.

13 Claims, 3 Drawing Sheets

US 6,200,475 B1

METHOD OF CONVERTING ORGANIC WASTE BY THERMOPHILIC FERMENTATION

BACKGROUND OF THE INVENTION

1. Field of the Present Invention

The present invention relates to a method of converting organic waste to usefull end product by aerobic thermophilic fermentation process within a short period of time by using porous material, which may contain cultivated thermophilic microorganisms, as a fermentation medium, and external heat to achieve thermophilic temperature.

2. Description of Related Arts

Large quantities of organic waste are produced from families and processing plants in the city and urban area everyday. Animal wastes are the largest source of both nitrogen and phosphorus pollution. It accounts for about more than half of total nitrogen loading and two-third of total phosphorous loading to the issue. As the production of livestock and poultry largely concentrated in certain regions and states, the air and water pollution problems have come along from the generation of manure. The most common methods include disposing organic waste to sanitary landfill and processing in composting facilities.

Due to the limited landfill spaces and the public resistance to new landfill, an alternative solution of waste problem becomes an urgent issue nowadays.

In fact, all organic wastes contain ambient nutrients for agriculture and animal feed industry. Composting manure and food residuals can reduce the biological activity and moisture. The organic matter in compost improves soil nutrient-holding and water-retaining capabilities which reduce fertilizer requirements and erosion while enhancing soil tilled. It also reduces odor and fly problem. While there are many benefits for composting, there is no promise to solve all manure and waste management problems. A composting operation takes time and money to manage and maintain. It will take extra land and mature time, usually from 3 weeks to 2 months. Compost windrows and storage facilities for raw materials will occupy large land and building space. With larger operations, composting becomes a very capital- and labor-intensive task. The most serious problem that can be developed with composting is run-off and odor pollution. If the compost pile contains too much nitrogen, ammonia odor becomes intolerable to neighbors. The excessive runoff and leachate are other potential pollution problems.

It is well known by using thermophilic microorganisms naturally present in the waste to dispose organic waste material. Pathogen and other contaminants in waste material are destroyed as the temperature raised up to 80° C. This method increases safety usage of the end products.

Several technologies have taught the using of thermophilic fermentation method to process organic wastes. For example, in U.S. Pat. Nos. 5,810,903 (1998), 5,702,499 (1997), 4,292,328 (1981), 4,132,638 (1979), 3,864,247 (1975), 3,838,198 (1974), 3,745,113 (1973), 3,462,275 (1969).

Some other technologies introduce the using of porous material to immobilize and proliferate microorganisms for wastewater treatment or other applications. For example, U.S. Pat. Nos. 5,863,789 (1999), 5,595,893 (1997), 5,240,611 (1993), 5,185,255 (1993), 5,180,495 (1993).

U.S. Pat. No. 5,810,903, issued to Branconnier et al, suggests a process for thermophilic aerobic fermentation organic waste. The fermentation process utilizes thermophilic microorganisms initiated over a period of time from 2 to 6 days. Then, the process that completely converts the organic waste to end products requires about 24 to 48 hours. This whole procedure requires complicated operation and equipment.

U.S. Pat. No. 5,702,499, issued to Timmenga, discloses a waste conversion by liquid thermophilic aerobic digestion. This method needs to carefully monitor and control the thermophilic digestion process for the determination of the length of the process. The 'end point' varies greatly with quality of the material processed and must be identified for each batch.

U.S. Pat. No. 4,292,328, issued to Coulthard et al, teaches a thermophilic aerobic digestion process for producing animal nutrients and other digested products. This method introduces air into the agitated mixture to bring temperature to at least 55° C. without using external heat and cause thermophilic microbial digestion of waste material. The complete process needs at least 4 days to complete.

U.S. Pat. No. 4,132,638, issued to Carlsson, suggests an aerobic thermophilic degradation with enzyme addition. Enzyme is added to promote degradation prior to preheated material. The degradation treatment takes 10 days to complete. The treatment has three critical factors needed to take care before process: particle size, dry matter, and pH must be satisfied.

U.S. Pat. No. 3,864,247, issued to Fuchs, discloses a biological decomposition of organic material by thermophilic microorganisms. This method does not use heat addition for thermophilic microbial activity. The process time needs 5 days.

U.S. Pat. 3,838,198, issued to Bellamy et al, introduces a conditioning raw waste input for digestion by thermophilic aerobic microorganisms. This method preheats material between 75° C. to 85° C. for a period of about 1 to 2 days. It does not mention the length of process time.

U.S. Pat. No. 3,745,113, issued to Fuchs et al, suggests a biological decomposition of organic material. This treatment brings heat to at least 42° C. by thermophilic microbial activity without external heat addition. It takes 6 to 10 days to process.

U.S. Pat. No. 3,462,275, issued to Bellamy, teaches a waste conversion process and product. The treatment utilizes a liquid medium with a thermophilic microorganism to convert waste.

U.S. Pat. No. 5,863,789, issued to Komatsu et al, discloses a microorganism-holding carrier and method for remediation of soil employing the carrier. This application uses hydrophilic polymer for holding microorganisms to manifest a biological action of microorganisms to remedy soil.

U.S. Pat. No. 5,595,893, issued to Pometto, III et al, suggests an immobilizing of microorganisms on a support made of synthetic polymer and plant material. This method uses synthetic polymer to immobilize microorganism to form a biofilm reaction for use in continuous formation in waste treatment system to remove contaminants and to reduce biochemical oxygen demand levels.

U.S. Pat. No. 5,240,611, issued to Burton, discloses an organic waste recycling system and method. This method utilizes porous material to treat liquid-borne organic waste.

U.S. Pat. No. 5,185,255, issued to Endo et al, suggests a cell culture method which uses porous material to proliferate microorganisms.

U.S. Pat. No. 5,180,495, issued to Thüer et al, suggests a water purification process which uses porous material populated by one or more microorganisms to purify water.

A common disadvantage of the above mentioned conventional arts is either the procedure is too complicated or needs more than 3 days to finish a complete process cycle or for water treatment purpose.

Although every patent presents a thermophilic method to process organic waste or uses porous material to carry microorganisms, none of them are designed to use porous material, which may contain cultivated thermophilic microorganisms, as a fermentation medium to decompose waste matters within 24 hours. Neither of these inventions offers an easy and simple operation procedure and low capital investment on equipment.

SUMMARY OF THE PRESENT INVENTION

It is an object of the present invention to provide a method of converting organic waste by thermophilic fermentation which is an innovative and improved method to decompose organic waste and produce useful end products at the same time. It substantially reduces the processing time to less than 12 hours. Since the fermentation is processed in thermophilic temperature, the end product is pathogen and weeds free.

It is another object of the present invention to provide a method of converting organic waste by thermophilic fermentation, which is an on-site waste solution to treat the organic waste within one day. The present invention prevents second pollution from using truck to move wastes to another site. It also reduces the burden of landfill and waste handling expenses.

It is another object of the present invention to provide a method of converting organic waste by thermophilic fermentation, which requires an affordable low capital investment on equipment. Farms can produce methane by themselves and use the methane to supply heat.

It is another object of the present invention to provide a method of converting organic waste by thermophilic fermentation to form useful end product that contains ambient nutrients and protein. The end product contains beneficial microorganisms that will provide a symbiosis and mutualism reaction to proliferate and grow beneficial microorganisms and control pathogen in the soil. This improves soil structure and nutrients that helps roots to grow. When it is used as animal feed supplements, the fermented product contains protein and other nutrients that improve animal digestion rate and then growth in better quality.

Accordingly, in order to accomplish the above objects, the present invention provides a method of converting organic waste to useful end product by aerobic thermophilic fermentation process within a short period of time by using porous material, which may contain cultivated thermophilic microorganisms, as a fermentation medium and external heat to achieve thermophilic temperature. The reader will see that the processing method of this invention can decompose organic waste into animal feed supplements or organic fertilizer within a short period of time and create sustainable environment. In addition, a distinctive feature of the present invention is to use porous material as a fermentation medium to create microbial symbiosis and mutualism reaction with microorganisms that naturally present in the organic waste. The microbial symbiosis and mutualism reaction proliferates and grows beneficial thernophilic microorganisms on the porous bed inside the porous material, and then accelerates organic waste fermentation and decomposition speed so as to decomposes organic waste into the useful end product within a short period of time.

Substantially, the present invention has several additional advantages as follows.

(a) Provide a sustainable environment solution.

(b) Merely require a short period of time to decompose organic waste, within 12 hours at most.

(c) Provide an on-site in-vessel waste solution with small land requirement.

(d) Provide a method to process larger volume than traditional in-vessel method.

(e) Provide a low capital investment to handle organic waste management.

(f) Provide an easy turnkey operation with less labor involved to handle organic waste management.

(g) Provide a processing method to prevent excessive nutrient run-off pollution and leachate problem.

(h) Produce a pathogen and weeds free end product.

(i) The end product is organic fertilizer or animal feed supplements with comfortable smell, so as to provide a farmer saves fertilizer or animal feeds expenses and earns extra income by selling organic fertilizer or animal feed supplements.

DETAILED DESCRIPTION OF THE PREFERRED EMBODIMENTS

Figure 1:
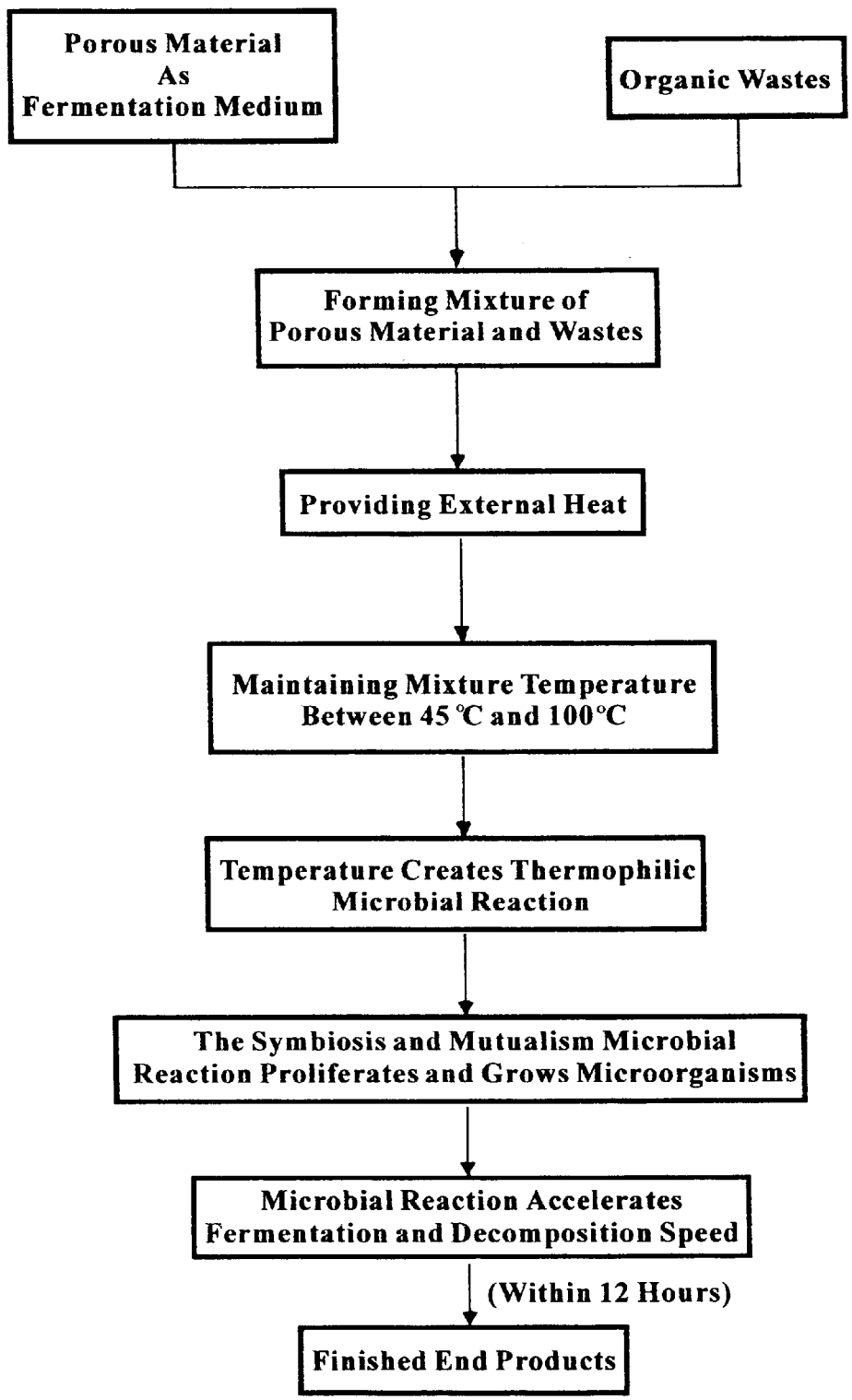
FIG. 1 is a block diagram of a method of converting organic waste by thermophilic fermentation according to a preferred embodiment of the present invention.

Referring to FIG. 1, a method of converting organic waste by aerobic thermophilic fermentation process according to a preferred embodiment of the present invention is illustrated, which comprises the following steps.

(1) Provide a predetermined amount of porous material.

(2) Mix an organic waste with the porous material, which may contain the cultivated thermophilic microorganisms, as a fermentation medium in a mixing digester to form a waste mixture.

(3) Heat the waste mixture to a thermophilic temperature between 45° C. and 100° C. by providing an external heat source to transfer heat into the waste mixture.

(4) Maintain the thermophilic temperature between 45° C. and 100° C. for microbial symbiosis and mutualism reaction to continuously proliferate and grow beneficial thermophilic microorganisms between the porous material and microorganisms naturally presented in the organic waste.

(5) Allow the microbial symbiosis and mutualism reaction to accelerate the speed of a fermentation and decomposition of organic waste until the organic waste is converted into a useful end product within a predetermined period of time.

In step (1), the porous material can be, but not limited to, charcoal, coal, oyster shell, clam shell, sea shell, egg shell, rice husk, corn husk, starch, bone, wood, feather, glass, ceramic, gypsum, porcelain, clay, diatomaceous earth, minerals, polymer, metal or a combination thereof.

Moreover, in step (1), the total weight of the porous material to be mixed with the organic waste is 1% to 10% (preferably 5%) of the weight of the organic waste to be converted. Besides, the thermophilic microorganisms are selected from the group comprising microorganisms culture of thermophilic Actinomycetales, thermophilic Pseudomonadales, thermphilic Eubacteiales, and thermophilic fungi.

In step (2), the present invention is specifically suitable for converting organic waste including animal manure, animal fecal matters, animal carcass, food wastes, food processing waste, green waste, and kitchen waste.

After step (2) and before step (3), the present invention can further comprise an additional step of adding water into the waste mixture to maintain a 60% to 70% moisture level.

In step (4), the waste mixture is agitated with heat in an aerobic condition and the odor produced during fermentation is sucked into a deodorizer before emitting to the atmosphere. Moreover, under the thermophilic temperature, between 45° C. and 100° C., the microbial symbiosis and mutualism reaction is conducted between the porous material that contains the cultivated thermophilic microorganism as the fermentation medium and microorganisms that naturally present in the organic waste, and that the microbial symbiosis and mutualism reaction proliferates and grows beneficial thermophilic microorganisms on the porous bed inside the porous material.

In step (5), the end product will be discharged when a moisture content thereof drops to about 30%.

Figure 2:
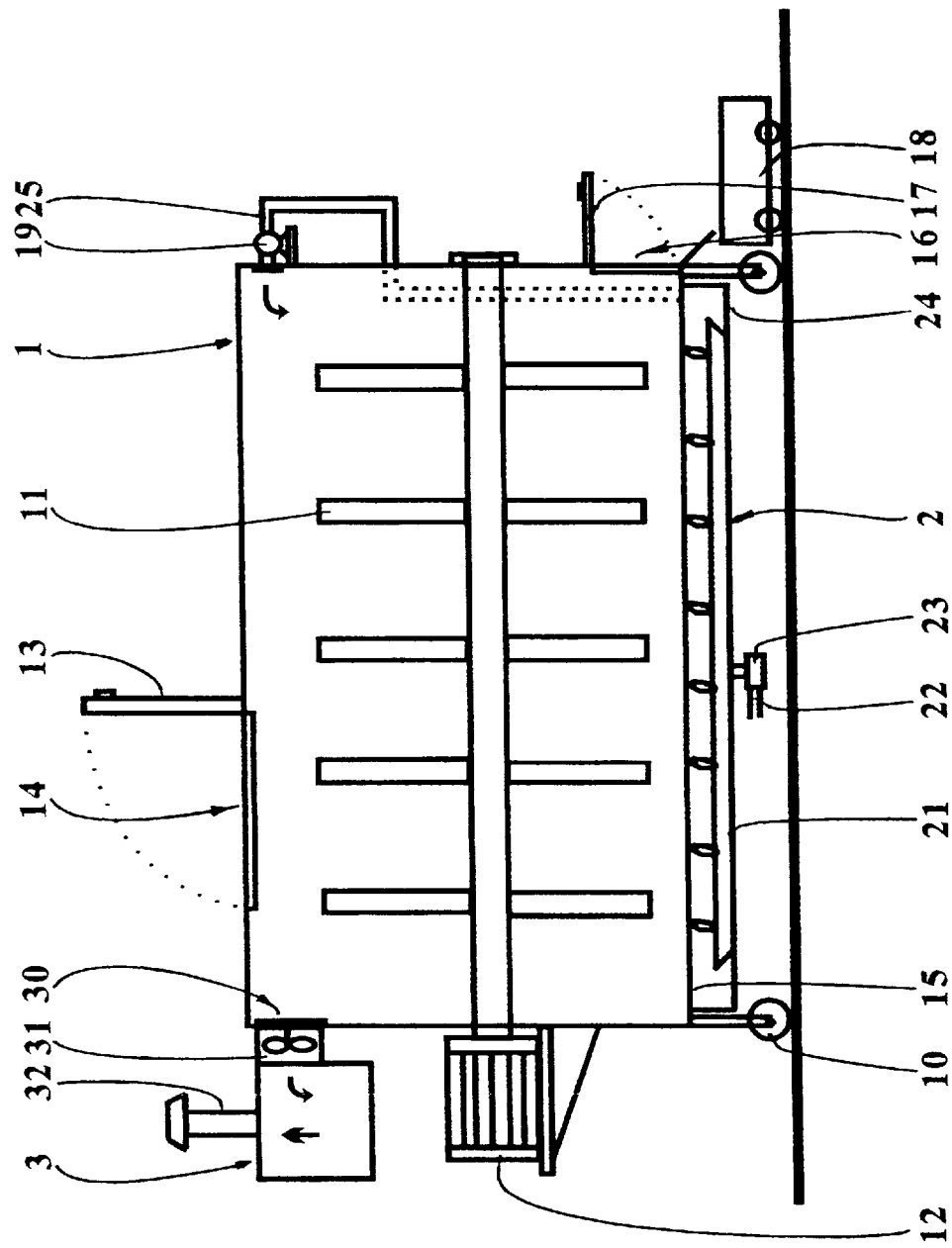
FIG. 2 is a schematic view of a mixing apparatus with blenders driven by a motor and with burner beneath the apparatus according to the above preferred embodiment of the present invention.

Referring to FIG. 2, the method of converting organic waste by aerobic thermophilic fermentation process can be processed within a mixing apparatus 1 as the mixing digester. The mixing apparatus 1 comprises a plurality of blenders 11 which is driven by a motor for mixing the organic waste that naturally contains microorganisms, such as animal manure, carcass, and kitchen waste, received in batch with the porous material as fermentation medium, which may contains the thermophilic microorganisms, to form a waste mixture.

A heat source 2 such as a burner 21 is installed beneath the mixing apparatus 1 to transfer heat to the waste mixture in the mixing apparatus 1. A receiving hole 14 is provided on a topside cover 13 of mixing apparatus 1. At least four wheels 10 are connected to a bottom 15 of mixing apparatus 1 for easy to move around. A discharge hole 16, which is provided at a corner of the bottom 15, can be closed by a discharge door 17. A conveyor or cart 18 is positioned adjacent to the discharge hole 16 to receive finished end products.

The mixing apparatus 1 further comprises an air pump 19 to suck hot fume through a pipe 25 which is extended from a heat fume cover 24 of the burner 21. The air pump 19 injects the hot fume into the mixing apparatus 1 for the purpose of supply hot air for aerobic fermentation, recover and recycle heat and reduce the surrounding room temperature.

The heat source 2, i.e. the burner 21, further comprises an inflow tube 22 for supplying heat to the waste mixture inside the mixing apparatus 1 and a temperature control device 23 for controlling the gas inflow so as to maintain the waste mixture inside the mixing apparatus 1 at a thermophilic temperature between 45° C. and 100° C.

The mixing apparatus 1 also comprises a deodorizer 3 connected to an outside wall of the mixing apparatus 1 for removing the odor of the gas produced during the process before emitting to the atmosphere, and a sucking fan 31 for sucking the processing odor through an air outflow pipe 30 into the deodorizer 3. Then, the clean air emits through an air outflow pipe 32 into the atmosphere.

Figure 3:
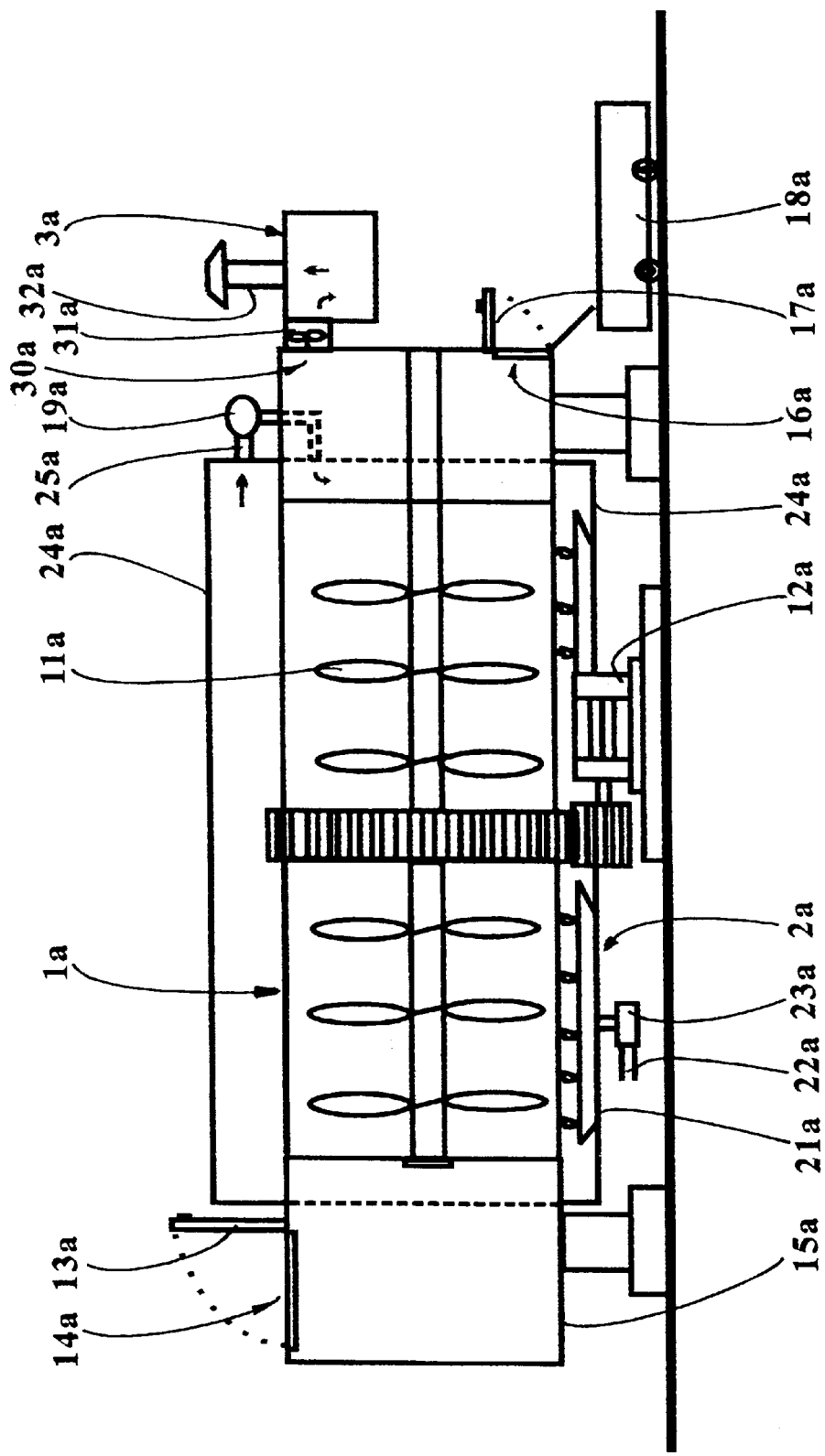
FIG. 3 is a schematic view of a rotary tank with blenders inside to mix the material and with burner beneath the rotary tank according to the above preferred embodiment of the present invention.

Referring to FIG. 3, the method of converting organic waste by aerobic thermophilic fermentation process can also be processed within a rotary tank 1a according to another embodiment of the mixing digester. The rotary tank 1a also comprises a plurality of blenders 11a therein and a rolling motor 12a for rolling the rotary tank 1a. A receiving hole 14a is located on a topside of the rotary tank 1a and a topside cover 13a is connected to the receiving hole 14a for covering the receiving hole 14a of the rotary tank 1a.

A discharge hole 16a with a discharge door 17a is provided at an opposite bottom 15a side of the receiving hole 14a. A heat source 2a, for example a burner 21a, is installed underneath the bottom 15a to transfer heat to the waste mixture in the rotary tank 1a. A conveyor or cart 18a is positioned closed to the discharge hole 16a to receive the end products.

The rotary tank 1a further comprises an air pump 19a for sucking hot fume through a pipe 25 extended from a heat fume cover 24a of the burner 21a. The air pump 19a injects the hot fume into the rotary tank 1a for the purpose of supply hot air for aerobic fermentation, recover and recycle heat and reduce the surrounding room temperature.

The heat source 2a, for example the burner 21a, also comprises an inflow tube 22a and supplies heat to the waste mixture inside the rotary tank 1a and a temperature control device 23a for controlling the gas inflow and the thermophilic temperature between 45° C. and 100° C.

A deodorizer 3a is connected to an outside wall of the rotary tank 1 which has a sucking fan 31a adapted to suck the processing odor through an air outflow pipe 30a into the deodorizer 3a. Then, the clean air emits through an air outflow pipe 32a into atmosphere.

According to the present invention, in order to start the process by means of the mixing apparatus 1 or the rotary tank 1a as shown in FIGS. 2 and 3 respectively, the porous material that contains cultivated thermophilic microorganisms is introduced into and mixed with the organic waste material to form the waste mixture in the mixing apparatus 1 or the rotary tank 1a through the receiving hole 14 or 14a, wherein the total weight of the porous material to be mixed with the organic waste is approximately 5% of the weight of the organic waste to be converted. If necessary, water can be added to the waste mixture to maintain at 60% to 70% moisture level at the staring point. The burner 21 or 21a transfers heat into the waste mixture. The flow and temperature control device 23 or 23a maintains the thermophilic temperature of the waste mixture between 45° C. and 100° C. The waste mixture is agitated with heat in an aerobic condition.

The thermophilic temperature brings microbial symbiosis and mutualism reaction between porous material that contains the cultivated thermophilic microorganism as the fermentation medium and microorganisms that naturally present in the organic waste. The microbial symbiosis and mutualism reaction proliferates and grows beneficial thermophilic microorganisms on the porous bed inside the porous material, and then accelerates organic waste decomposition speed so as to decompose the organic waste into useful end product within a short period of time. The odor during fermentation is sucked into the deodorizer 3 or 3a through the sucking fan 31 or 31a. As moisture content drops to about 30%, the end product is discharged. The end products are discharged through the discharged hole 16 or 16a to the conveyor or cart 18 or 18a to pile up or bag for market.

Preferably, the structure of porous material is open porosity with high surface area to volume ratio. The thermophilic microorganism cultivates on the porous bed inside the porous material.

As mentioned above, the process is preferably to adjust the moisture level between 60% to 70% at the starting point. The process operates over wide range of pH level without the addition of pH adjusting agents.

The mixing digester can be all kinds of aerobic mixing during processing. It can be a mixing apparatus, rotary tank, and mixing bay. The mixing apparatus may be a mixing container with and without blenders and the rotary tank can selectively comprise immobilized and rotated blenders. A mixing bay may comprise a building structure with turner consisting of open roof and enclosed roof and open wall and enclosed wall.

Furthermore, it is possible to operate process batch, semi-continuous, and continuous basis. As each mixing digester connects to each other with conveyer, the single batch process becomes semi-continuous or continuous basis. As rotary tank has enough length, correct RPM, and flow angel, the process is continuous basis.

Moreover, the external heat source includes all kind of energy sources, like natural gas, propane, methane, electricity, steam, or solar energy. The mixture temperature prefers to maintain between 45° C. and 100° C. to conduct microbial symbiosis and mutualism reaction between the porous material that contains the cultivated thermophilic microorganism as the fermentation medium and the microorganisms that naturally present in the organic waste. The microbial symbiosis and mutualism reaction proliferates and grows beneficial thermophilic microorganisms on the porous bed inside the porous material, and then accelerates organic waste decomposition speed so as to decompose the organic waste into useful end product within a short period of time.

The deodorizer 3, 3a contains water pump, damp wood slice, activated charcoal or coal to deodorize odor before emitting to atmosphere.

In view of above, the end product is pathogen and weeds free since the process is under thermophilic temperature. The end products from organic waste are typically dry, granular, powdery and contain different nutrients and protein. Besides using as fertilizer, it is suitable for feeding to animal as part of animal's nutrient diet.

In order to further illustrate the features of the present invention, an experimental example is introduced thereafter. The process is performed with about 15 cubic yard chicken manure, 10 chicken carcass, 20 pounds of fish waste, and 20 pounds vegetable wastes. All of the organic wastes are mixed with the porous material, about 5% by solid weight, which contains cultivated thermophilic microorganisms inside of mixing apparatus. A gas infrared burner is installed underneath the mixing digester to transfer heat into the waste mixture. The waste mixture moisture level maintains around 60% to 70% when started. The blenders mix the mixture during processing to maintain aerobic condition. The mixture temperature arrives to a thermophilic temperature at 45° C. to 50° C. one hour later after started. Two hours later, the thermophilic temperature rises to 70° C. Some feathers are taken off from the chicken body; some carcasses have already divided into pieces. The decomposition rate is roughly about 10% to 15%. Four hours later, the thermophilic temperature arrives to 90° C. All vegetables and fishes are decomposed. The chicken carcass has already been decomposed around 50% to 60%. The nuisance odor smell of chicken manure has disappeared. Six hours later, decomposition finished. There are only very few bones left over. The decomposition rate is about 99%.

The end product has medium powder size with light brown color and comfortable smell. The end product is a very good organic fertilizer that contains a N-P-K of 2.3–0.6–4.0 and a C/N ratio of 11.

Although the description above contains many devices, these should not be constructed as limiting the scope of the invention but as merely providing explanation of some of the presently preferred devices of this invention. Rather than by the examples given, the invention includes all embodiments, which are functional or mechanical equivalents of the specific embodiments, and features that have been described and illustrated herein. Furthermore, it is intended that the invention covers all alternative embodiments as may be within the scope of the following claim.

What is claimed is:

1. A method of converting organic waste by thermophilic fermentation, comprising steps of;
   (a) providing a predetermined amount of porous material as a fermentation medium, wherein a predetermined amount of thermophilic microorganisms is provided in said porous material and said thermophilic microorgaanism are one or more members selected from the group comprising thermophilic Actinomycetales, thermophilic Pseudomonadales, thermophilic Eubacteriales, and thermophilic fungi;
   (b) mixing said porous material wit an organic waste that naturally contains microorganisms in a mixing digester to form a waste mixture
   (c) heating said waste mixture to a thermophilic temperature between 45° C. and 100° C. by providing an extemal heat source to transfer heat into said waste mixture;
   (d) maintaining said thermophilic temperature between 45° C. and 100° C. for microblid symbiosis and mutualism reaction between said porous material and said microorganisms naturally contained in said organic waste so as to continuously proliferate and grow beneficial thermophilic microoranIsms inside said porous material; and
   (e) allowing said microbial symbiosis and mutualism reacfion to accelerate a speed of a fermentation and decomposition of said organic waste until said organic waste is converted into a useful end product within a predetermined period of time.

2. A method of converting organic waste by thermophilic fermentation, as recited in claim 1, wherein said porous material is one or more material selected from the group comprising charcoal, coal, oyster shell, clam shell, sea shell, egg shell, rice husk, corn husk, starch, bone, wood, feather, glass, ceramic, gypsum, porcelain, clay, diatomaceous earth, minerals, polymer, and metal.

3. A method of converting organic waste by thermophilic fermentation, as recited in claim 1, wherein said organic waste are one or more members selected from the group comprising animal manure, animal fecal matters, animal carcass, food wastes, food processing waste, green waste, and kitchen waste.

4. A meod of converting organic waste by thermophilic fermentation, as recited in claim 2, wherein said organic waste are one or mrom members selected from the group comprising animal manure, animal fecal matters, animal carcass, food wastes, food processing wast, green waste, and kitchen waste.

5. A method of converting organic waste by thermophilic fermentation, as recited in claim 1, wherein a total weight of said porous material to be mixed with said organic waste is 1% to 10% of a weight of said organic waste to be converted.

6. A method of converting organic waste by thermophilic fermentation, as recited in claim 4, wherein a total weight of said porous material to be mixed with said organic waste is 1% to 10% of a weight of said organic waste to be converted.

7. A method of converting organic waste by thermophilic fermentation, as recited in claim 1, after the step (b) and before the step (c), further comprising an additional step of adding water into said waste mixture to maintain a 60% to 70% moisture level.

8. A method of converting organic waste by thermophilic fermentation, as recited in claim 4, after the step (b) and before the step (c), further comprising an additional step of adding water into said waste mixture to maintain a 60% to 70% moisture level.

9. A method of converting organic waste by thermophilic fermentation, as recited in claim 6, after the step (b) and before the step (c), further comprising an additional step of adding water into said waste mixture to maintain a 60% to 70% moisture level.

10. A method of converting organic waste by thermophilic fermentation, as recited in claim 4, wherein, in the step (d), said waste mixture is agitated with heat in an aerobic condition and an odor produced during fermentation is sucked into a deodorizer before emitting to the atmosphere.

11. A method of converting organic waste by thermophilic fermentation, as recited in claim 9, wherein, in the step (d), said waste mixture is agitated with heat in an aerobic condition and an odor produced during fermentation is sucked into a deodorizer before emitting to the atmosphere.

12. A method of converting organic waste by thermophilic fermentation, as recited in claim 1, wherein said mixing digester comprises a mixing apparatus which comprises a plurality of blenders which is driven by a motor for mixing said organic waste received in batch with said porous material containing fermentation medium to form said waste mixture; a heat source being installed beneath said mixing apparatus to transfer heat to said waste mixture in said mixing apparatus, a receiving hole being provided on a topside cover of mixing apparatus, a discharge hole which is closed by a discharge door being provided at a corner of a bottom for discharging said end products, wherein said mixing apparatus further comprises an air pump to suck a hot fume through a pipe which is extended from a heat fume cover of said heat source, said air pump injecting said hot fume into said mixing apparatus for supplying hot air for aerobic fermentation, recovering and recycling heat and reducing a surrounding room temperature, said heat source further comprising an inflow tube for supplying heat to said waste mixture inside said mixing apparatus and a temperature control device for controlling said gas inflow so as to maintain said waste mixture inside said mixing apparatus at said thermophilic temperature between 45° C. and 100° C., said mixing apparatus further comprising a deodorizer connected to an outside wall of said mixing apparatus and a sucking fan for sucking a processing odor through an air outflow pipe into said deodorizer before emitting into atmosphere.

13. A method of converting organic waste by thermophilic fermentation, as recited in claim 1, wherein said mixing digester comprises a rotary tank which comprises a plurality of blenders therein and a rolling motor for rolling said rotary tank a heat source being installed beneath said mixing apparatus to transfer heat to said waste mixture in said mixing apparatus, a receiving hole being provided on a topside cover of mixing apparatus, a discharge hole which is closed by a discharge door being provided at a corner of a bottom for discharging said end products, wherein said mixing apparatus further comprises an air pump to suck a hot fume through a pipe which is extended from a heat fume cover of said heat source, said air pump injecting said hot fume into said mixing apparatus for supplying hot air for aerobic fermentation, recovering and recycling heat and reducing a surrounding room temperature, said heat source further comprising an inflow tube for supplying heat to said waste mixture inside said mixing apparatus and a temperature control device for controlling said gas inflow so as to maintain said waste mixture inside said mixing apparatus at said thermophilic temperature between 45° C. and 1000° C., said mixing apparatus further comprising a deodorizer connected to an outside wall of said mixing apparatus and a sucking fan for sucking a processing odor through an air outflow pipe into said deodorizer before emitting into atmosphere.

* * * * *